(12) United States Patent
Bengtsson et al.

(10) Patent No.: US 11,745,042 B2
(45) Date of Patent: Sep. 5, 2023

(54) EXERCISE MACHINE MONITORING SYSTEM FOR MONITORING ONE OR MORE EXERCISE MACHINES

(71) Applicant: SONY CORPORATION, Tokyo (JP)

(72) Inventors: Henrik Bengtsson, Lund (SE); Magnus Hallqvist, Lund (SE); Anders Fredlund, Lund (SE); Johan Nyman, Lund (SE); Tomas Jönsson, Lund (SE); Johan Alvå, Lund (SE); Anders Linge, Lund (SE); Johan Helgertz, Lund (SE); Johan Apelqvist, Lund (SE); Jens Rydberg, Lund (SE); Peter Larsson, Lund (SE)

(73) Assignee: SONY CORPORATION, Tokyo (JP)

( * ) Notice: Subject to any disclaimer, the term of this patent is extended or adjusted under 35 U.S.C. 154(b) by 330 days.

(21) Appl. No.: 16/957,049

(22) PCT Filed: Dec. 3, 2018

(86) PCT No.: PCT/SE2018/051242
§ 371 (c)(1),
(2) Date: Jun. 22, 2020

(87) PCT Pub. No.: WO2019/147174
PCT Pub. Date: Aug. 1, 2019

(65) Prior Publication Data
US 2020/0342975 A1    Oct. 29, 2020

(30) Foreign Application Priority Data

Jan. 24, 2018 (SE) .................................... 1850079-3

(51) Int. Cl.
*A63B 21/062* (2006.01)
*A63B 24/00* (2006.01)
*A63B 71/06* (2006.01)

(52) U.S. Cl.
CPC ...... *A63B 21/0628* (2015.10); *A63B 24/0062* (2013.01); *A63B 71/0619* (2013.01);
(Continued)

(58) Field of Classification Search
CPC ............ A63B 2225/50; A63B 2225/52; A63B 2225/54; A63B 2220/10; A63B 2220/13;
(Continued)

(56) References Cited

U.S. PATENT DOCUMENTS

2003/0211916 A1   11/2003 Capuano
2014/0142459 A1*  5/2014 Jayalth .................. A61B 5/318
                                                           600/547
(Continued)

FOREIGN PATENT DOCUMENTS

EP          3373190 A1     9/2018
WO      2015113162 A1      8/2015
(Continued)

OTHER PUBLICATIONS

European Office Action from corresponding European Application No. 18821764.0, dated Feb. 9, 2021, 5 pages.
(Continued)

*Primary Examiner* — Sundhara M Ganesan
*Assistant Examiner* — Zachary T Moore
(74) *Attorney, Agent, or Firm* — TUCKER ELLIS LLP

(57) ABSTRACT

The disclosure relates generally to devices, systems and methods for measuring, transmitting, recording and displaying information relating to physical exercise and, more particularly, to a monitoring system for monitoring exercise machines comprising a lifting mechanism for selectively engaging one or more of the weights. A first aspect of the disclosure relates to an exercise machine monitoring system for monitoring exercise machines, where the exercise machines, comprise a plurality of stacked weights, the
(Continued)

monitoring system comprises, for each of the exercise machines a repetition detector and an exercise machine identifier. The monitoring system further comprises an observer and a user device.

14 Claims, 8 Drawing Sheets

(52) U.S. Cl.
CPC ..... *A63B 2220/20* (2013.01); *A63B 2220/833* (2013.01); *A63B 2225/50* (2013.01)

(58) Field of Classification Search
CPC ............ A63B 2220/17; A63B 2220/20; A63B 2220/31; A63B 2220/62; A63B 2220/80; A63B 2220/801; A63B 2220/803; A63B 2220/83; A63B 2220/833; A63B 24/0003; A63B 24/0006; A63B 24/0062; A63B 24/0075; A63B 24/0087; A63B 2024/0065; A63B 2024/0068; A63B 2024/0071; A63B 2024/0078; A63B 2024/0081; A63B 2024/009; A63B 2024/0093; A63B 2024/0096; A63B 21/06; A63B 21/062; A63B 21/0626; A63B 21/0628; A63B 21/063; A63B 21/0632

See application file for complete search history.

(56) References Cited

U.S. PATENT DOCUMENTS

| | | | | |
|---|---|---|---|---|
| 2014/0235409 | A1* | 8/2014 | Salmon | A63B 21/0724 482/8 |
| 2014/0363800 | A1* | 12/2014 | Harris | G09B 19/0038 434/247 |
| 2015/0265903 | A1* | 9/2015 | Kolen | G16H 40/67 700/91 |
| 2016/0346617 | A1* | 12/2016 | Srugo | A63B 24/0087 |
| 2017/0173392 | A1* | 6/2017 | Orfield | A63B 21/0628 |

FOREIGN PATENT DOCUMENTS

| | | |
|---|---|---|
| WO | 2017125787 A1 | 7/2017 |
| WO | 2017178048 A1 | 10/2017 |

OTHER PUBLICATIONS

Swedish Search Report from corresponding Swedish Application No. 1850079-3, dated Sep. 27, 2018, 3 pages.
International Search Report and Written Opinion from corresponding International Application No. PCT/SE2018/051242, dated Jan. 29, 2019, 9 pages.

* cited by examiner

EXERCISE MACHINE MONITORING SYSTEM FOR MONITORING ONE OR MORE EXERCISE MACHINES

TECHNICAL FIELD

The invention relates generally to devices, systems and methods for measuring, transmitting, recording and displaying information relating to physical exercise and, more particularly, to a monitoring system for monitoring exercise machines comprising a lifting mechanism for selectively engaging a number of weights.

BACKGROUND

In recent years, there has been a virtual explosion in the popularity of exercise and physical fitness. There are many popular forms of physical exercise including, for example, running, bicycling, and weight training. The growing interest in weight training is reflected by the growing number of gyms found in both public and private settings.

There are various types of weight training equipment. Typical weight machines, for example, use gravity as the primary source of resistance. A combination of simple machines (e.g., pulleys, levers, wheels, inclines, etc.) to change the mechanical advantage of the overall machine relative to the weight and convey the resistance to the person using the exercise machine. Conventional stacked weight machines, such as those made by Cybex International, Inc. and Nautilus, Inc., typically include a stack of rectangular weight plates through which a lifting mechanism, e.g. comprising a vertical lifting bar, passes. The lifting bar includes a plurality of holes configured to accept an engaging member, such as a pin. Each of the plates has a corresponding channel that aligns with one of the holes in the lifting bar when the lifting bar is in the lowered or at-rest position. To lift a selected number of the plates, the user operates the engaging member, e.g. by inserting a pin through the channel and the corresponding hole in the lift bar at a selected weight level. As the user goes through the exercise motion, the lift bar rises and the engaging member supports all of the plates stacked above it. The various settings on the weight machine allow the user to select from several different levels of resistance over the same range of motion by simply inserting the pin into the lift bar at a desired weight level. Conventional weight pins usually include a cylindrical shaft made of stainless steel or other hard metal. In its simplest form, a weight pin can be made from a single piece of cylindrical metal rod that is bent slightly at one end to form a handle for inserting and removing the pin into a weight stack. Other types of weight pins can include a plastic or metal handle portion that is attached to the cylindrical shaft which is inserted into the weight stack. The shaft can include spring-loaded ball bearings and/or other locking features to releasable engage the pin with the weight stack and prevent it from becoming dislodged during use of the weight machine. Some pins with locking features include a push button on the handle to facilitate engagement of the locking feature with the weight stack and/or lifting bar.

One important aspect of any type of exercise program is the ability to track personal performance and progress. For example, people engaged in endurance or distance forms of exercise (e.g., running, swimming, bicycling, etc.) often track the distance and/or time associated with a particular run, swim, ride, etc. Similarly, people using cardiovascular exercise machines (e.g., treadmills, stair-steppers, stationary bicycles, etc.) are often interested in knowing how long they exercise or how many calories they burn during a particular session.

One shortcoming of conventional weight machines, is however, that they lack a convenient way for the user to track and record his or her progress on a particular machine or group of machines during a particular exercise session or over a given period of time. As a result, people engaged in weight training programs often rely on memory to keep track of how many weights they lifted on a particular occasion, or how many repetitions they performed on a particular machine. Rather than rely on memory, some people use notebooks to manually record information about their workout. Neither of these approaches, however, is particularly convenient.

In this context, a system for tracking workout related information was suggested in WO2015/113162A1. That system includes a wearable device wirelessly connectable to receive workout information related to use of a workout equipment, including a weight being used in the workout equipment. Workout information is collected by means of a weight stack selector device, which may determine both selected weight information and repetition information based on distance measured from a weight stack selector device to a stationary reference point. This may be accomplished by means of a transmitter incorporated in the selector device. However, the system proposed in WO2015/113162A1 relies on that a user possesses a wearable device, in order for the collection of work out information to take place.

Furthermore, a general problem related to systems for measuring and tracking workout data is power consumption. In a gym, exercise machines are typically spread out on the floor throughout one or more rooms, and access to a mains outlet is rarely available at each machine. The system is therefore preferably battery-charged, and moderate power consumption is consequently an overall objective. Furthermore, even if an exercise machine is intended to be used in a certain manner, gym users tend to find new ways of exercising using such machines. The measurement system should be so devised that minimum user interaction is required, and such that accidental tampering or inhibition of the measurement is prevented during foreseeable use of the exercise machine.

In conclusion, there is a strong digitization trend in the gym industry. Several vendors are building machines with built-in reps and weight measurements. However, exercise machines with built-in measurements are expensive, they commonly require built-in display and AC power and has no natural interaction with the user's mobile phone.

SUMMARY

A solution where old exercise machines can be kept and the digitization can be retrofit, and which the individual exercise machines do not require AC power is what many gyms and machine vendors strive for. Therefore, an object of embodiments herein is to provide a system for monitoring exercise machines that is robust, easy to install, power efficient, that provides a good user experience for users and where the users do not need any additional hardware. A further objective is to provide a monitoring system that can provide data to gym owners in order to enable gym owners to use of the data to analyze activities in the gym.

Users use their mobile phones in the gym for many reasons, such as music, social media, gym programs, etc. A solution where the phone connects to the exercise machines seamlessly, is therefore proposed.

A first aspect of the disclosure relates to an exercise machine monitoring system for monitoring a plurality of exercise machines, where the exercise machines, comprise a plurality of stacked weights. The monitoring system further comprises, for each of the exercise machines a repetition detector and an exercise machine identifier. The monitoring system further comprises an observer and a user device. The repetition detector is configured to be arranged to the stacked weights and to broadcast a short-range wireless communication signal comprising an identity of the exercise machine and an indication of a vertical movement of at least one of the stacked weights. The exercise machine identifier is configured to transmit a near field wireless communication signal comprising the identity of the exercise machine (i.e. an exercise machine identity). The observer is configured to receive the short-range wireless communication signals broadcasted by repetition detectors and to generate the exercise data based on the received short range wireless communication signals. In some embodiments, the observer is configured to be arranged centrally in the gym. The user device is configured to receive a near field wireless communication signal transmitted by one of the repetition detectors, to retrieve the exercise data generated by the observer corresponding to an exercise machine identity comprised in the received near field wireless communication signal and to provide the retrieved exercise data or information associated therewith to a user. The proposed monitoring system is robust and easy to install as no cables are required. Furthermore, the monitoring system is power efficient and it a can be retro-fitted to existing gyms using their old machines. The monitoring system does not require any external power, but the devices may be provided with their own power sources, typically batteries. Because observers are typically placed centrally in the gym, the short-range wireless communication signals may be broadcasted with low energy, whereby the batteries may last long.

In some embodiments, the observer is configured to generate exercise data in real-time and wherein the user device is configured to retrieve the generated data and to provide it to the user in real-time. This provides a nice user experience for users.

In some embodiments, the monitoring system further comprises a weight sensing device configured to sense a weight of the stacked weights that perform the vertical movement, and then the short-range wireless communication signal further comprises an indication of the sensed weight. Thus, the users may track both repetitions of an exercise and corresponding weight used in the exercise.

In some embodiments, the observer is comprised in the user device and the user device is configured to retrieve the exercise data directly from the observer. This embodiment can operate even under bad network coverage, which might be the case for many gyms that are e.g. situated in basements etc.

In some embodiments, the monitoring system further comprises a server having access to the data storage, the server being configured to receive the exercise data from the observer then user device is configured to retrieve the exercise data from the server. In the server data from multiple users and machines are stored. Thus, insights and knowledge can be generated for both users and the gym owners. The server may collect and save data representing all exercise performed in a gym. This data may be used to learn how the gym users utilize the exercise machines. The data is collected independent on whether any users have logged into the machines.

In some embodiments, the user device is configured to retrieve broadcasted exercise data from the server.

In some embodiments, the user device is configured to receive broadcasted exercise data directly from the repetition detector and to combine exercise data received directly from the repetition detector with exercise data retrieved from the server.

In some embodiments, the user device is configured to present enhanced exercise data obtained by combining exercise data received directly from the observer with exercise data received from the server, to the user.

In some embodiments, the observer is configured to generate exercise data in real-time and wherein the user device is configured to retrieve the generated data and to present it to the user in real-time.

In some embodiments, the user device is configured to present the exercise data on a display of the user device.

In some embodiments, the near field wireless communication signal is an NFC signal.

In some embodiments, the short-range wireless communication signal is a low energy signal.

In some embodiments, the short-range wireless communication signal is a Bluetooth Low Energy, BLE, signal.

In some embodiments, the user device is a smartphone.

According to a second aspect the disclosure relates to a method for monitoring a plurality of exercise machines arranged in a gym, wherein each of the exercise machines comprise a plurality of stacked weights, wherein each stacked weight comprises a repetition detector continually broadcasting a short-range wireless signal comprising an exercise machine identifier and an indication of a vertical movement of at least one of the stacked weights. The method comprising receiving, by a user device, a near filed wireless communication signal, transmitted by an exercise machine identifier of one of the exercise machines, comprising the exercise machine identity, and sending, by the user device, the user identity and an exercise machine identity, to a server and/or to other user devices. The method further comprises receiving, by one or more observers arranged centrally in the gym, short-range wireless signals broadcasted by the repetition detectors of the exercise machines, sending the received exercise data from the one or more observers to a server, and retrieving, by the user device, exercise data corresponding to an exercise machine identity comprised in the received near filed wireless signal for provision to a user.

In some embodiments, the method further comprises retrieving, comprises retrieving the exercise data from the server and/or directly from a repetition detector of the exercise machine corresponding to the exercise machine identity.

In some embodiments, the method comprises combining exercise data received directly from the observer with exercise data received from the server.

DETAILED DESCRIPTION

Figure 1A:
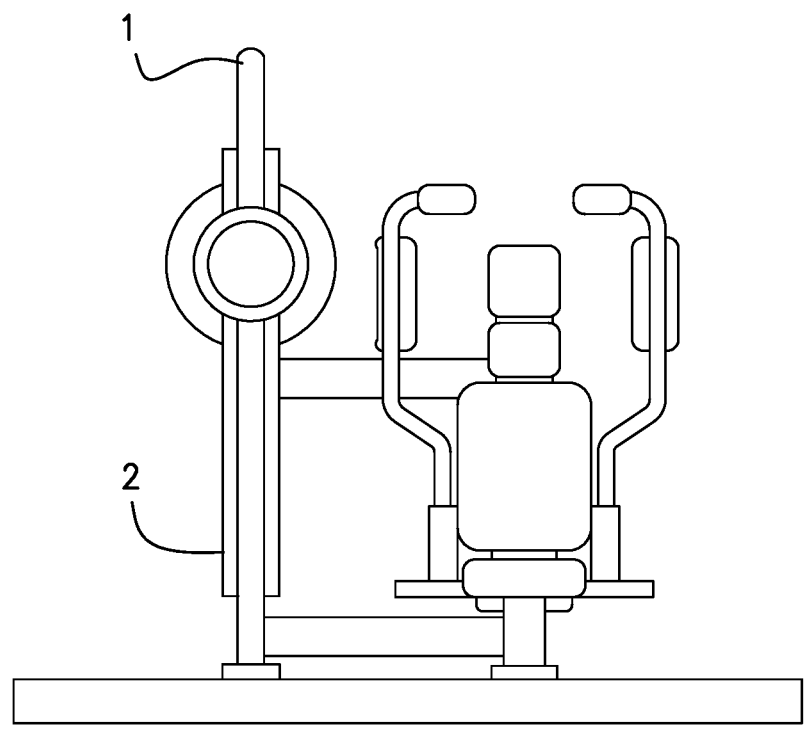
FIGS. 1a and 1b illustrates an exercise machine 1 that may be monitored using the proposed monitoring system.

Embodiments will now be described with reference to the drawings, wherein like reference numerals are used to refer to like elements throughout. It will be understood that the figures are not necessarily to scale. Also, features that are described and/or illustrated with respect to one embodiment may be used in the same way or in a similar way in one or more other embodiments and/or in combination with or instead of the features of the other embodiments.

Figure 1B:
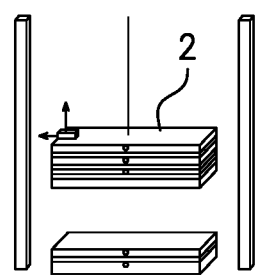

FIG. 1a is an isometric view of a stacked weight exercise machine 1 having a plurality of weights 2 which may be monitored using the proposed monitoring system. In FIG. 1b the stacked weights are shown in further detail.

Figure 2:
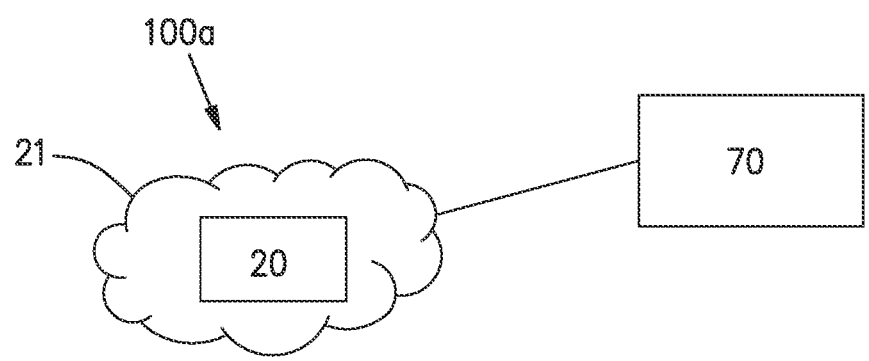
FIG. 2 illustrates a first example embodiment of the monitoring system.
Figure 2:
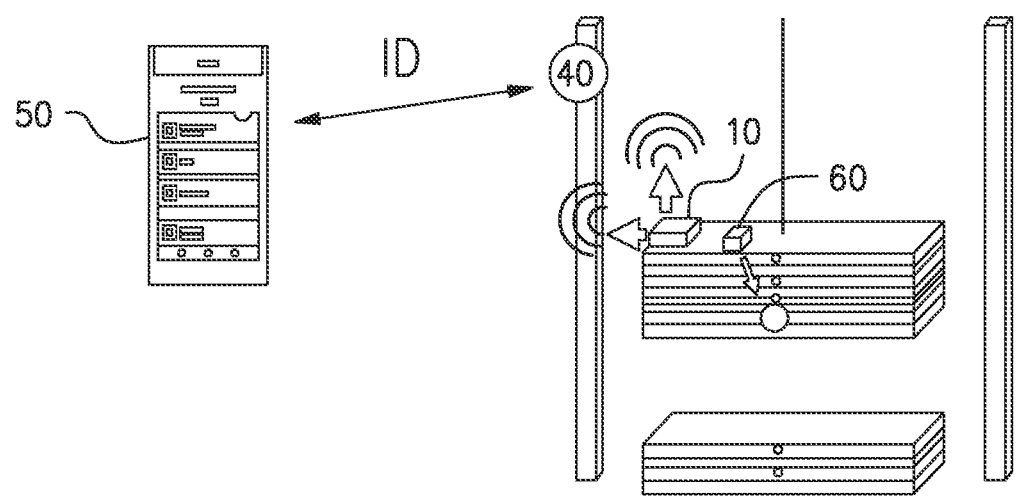

A first example implementation (denoted 100a) of the proposed monitoring system 100 for monitoring one or more exercise machines is shown in FIG. 2. In this example, only one exercise machine 1 is shown. However, it must be appreciated that the monitoring system would typically be arranged to monitor a plurality of exercise machines. The monitoring system 100a of FIG. 2 comprises one repetition detector 10 and one exercise machine identifier 40 for each exercise machine that is to be monitored. The monitoring system 100a further comprises a server 2, at least one observer 30, and a wireless communication device 50, a weight sensing device 60 and an admin tool 70. The server has access to a data storage 20.

Figure 3:
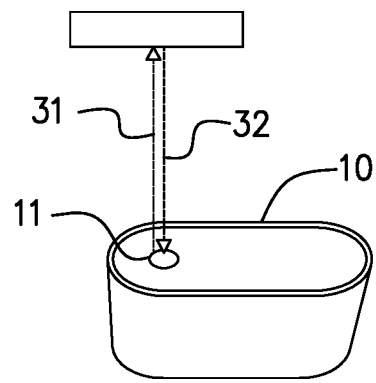
FIG. 3 illustrates a repetition detector in further detail.
Figure 5A:
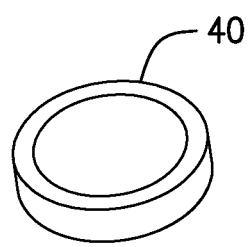
FIG. 5a illustrates an exercise machine identifier in further detail.
Figure 5B:
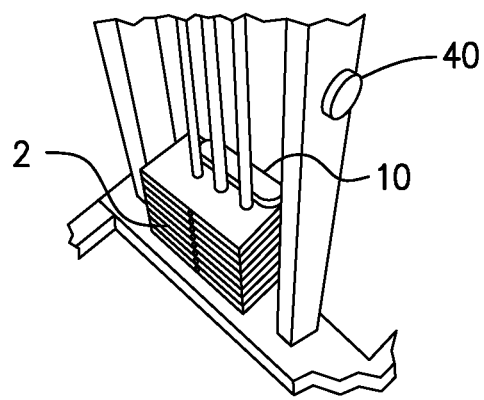
FIG. 5b illustrates the exercise machine identifier and the repetition detector when mounted.

FIG. 3 shows the repetition detector 10, also referred to as a main unit, in further detail. The repetition detector 10 is configured to be arranged to the stacked weights 2 of exercise machine 1. For example, it is configured to be arranged on the top of the stack of weights i.e. on the uppermost weight (FIG. 5b).

The repetition detector 10 advertises information (e.g. a series of integers) associated with the exercising using short range wireless communication.

More specifically, the repetition detector 10 comprises a sensor arrangement 11 configured to provide sensor data indicative of a vertical movement of at least one of the stacked weights 2. In exercise machines comprising stacked weights, the user may typically select how many of the weights should be used or engaged in the exercise. This is e.g. done by inserting a pin in one of the weights 2. During exercise, the user will then indirectly "lift" the selected weights, which corresponds to a vertical movement of the selected weights. The training may be tracked by monitoring how many weights are selected to be lifted and how many times the selected weights are lifted.

In other words, the repetition detector 10 comprises a sensor arrangement 11 configured to detect when a user performs an exercise in the exercise machine 1, by detecting vertical movements (herein also referred to as repetitions) of at least one of the stacked weights 2. The sensor arrangement 11 may e.g. comprise an accelerometer, range finder, a tension meter and/or similar. In an example implementation, the sensor arrangement 11 comprises a light range finder. The light range finder is configured to transmit a laser beam 31 and to receive a reflection 32 of the transmitted laser beam to determine the distance to a fixed point of the upper part of the exercise machine. For example, the rangefinder operates on the time of flight principle by sending a laser pulse in a narrow beam towards the object and measuring the time taken by the pulse to be reflected off the target and returned to the sender.

Detection of a vertical movement of the stacked weight would then typically correspond to detecting that the distance between the repetition detector 10 and the exercise machine has changes a pre-determined amount, which corresponds to that the stacked weights 2 lave been lifted. It is also possible to detect that at least one of the stacked weights 2 have moved more than a pre-determined distance upwards and then starts moving in the opposite direction.

The repetition detector 10 further comprises a short-range wireless communication interface. The short-range wireless communication interface e.g. uses Bluetooth Low Energy, BLE, ZigBee, LoRa.

The repetition detector 10 further comprises control circuitry configured to detect a vertical movement based on the sensor data provided by the sensor arrangement 11. The control circuitry is further configured to broadcast, using the short-range wireless communication interface, a signal (i.e. an advertisement) comprising an identity of the exercise machine 1 and an indication of the detected vertical movement of at least one of the stacked weights 2. That the signal is broadcasted means that it may be heard by multiple receivers. Typically, it can be heard by any observer 30 or user device 50 that supports the short-range communication protocol. The broadcasted signal comprise may also comprise other data such as a sequence number and/or repetition number or other information.

In other words, the repetition detector 10 serves as a broadcaster. A broadcaster does typically nothing more than transmitting data to its surroundings. It does so by advertising, and usually has useful data in the advertising packet, data that is meant for everyone to see. Such a device does not require a receiver, as its only role is to broadcast to others, so it never accepts connections.

For this type of applications low power consumption is crucial. Thus, in some embodiments the control circuitry is also configured to implement a power control function. The repetition detector 10 is then set in a sleep mode (which corresponds to practically completely switched off) when no exercise is performed, i.e. when the repetition detector 10 (and the stacked weights 2) are not moving. An accelerometer or similar is then used to wake-up the repetition detector 10 when it starts moving. The sensor arrangement 11 is then activated and starts detecting repetitions. If the repetition detector 10 is still for more than a few seconds, it will return to sleep mode.

The detection and broadcasting are typically performed in real-time, such that each and every repetition that a user performs in the exercise machine is "reported". Thus, it is important that each and every signal can be correctly observed. Therefore, in one example implementation the broadcasted signal comprises a pulse-train of ten repeated signals.

Figure 7:
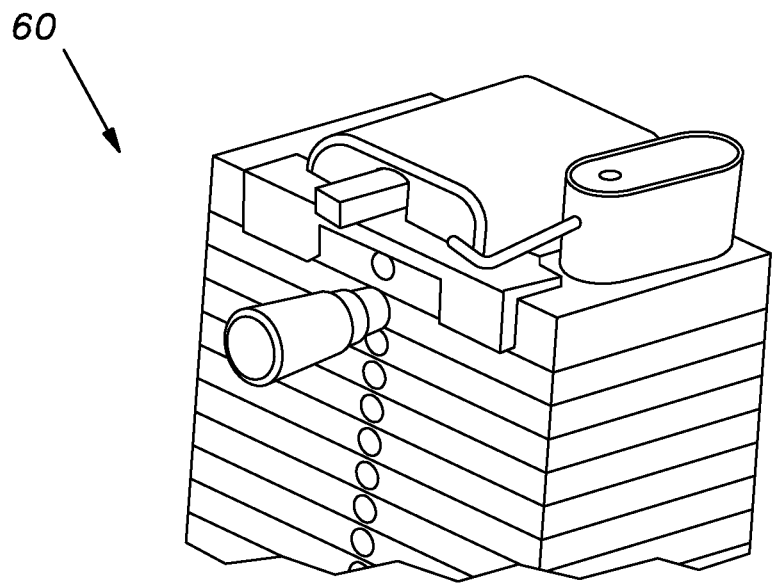
FIG. 7 illustrates the weight sensing device.

In some embodiments, the repetition detector 10 also comprises or is connected to a weight sensing device 60 (FIG. 7) The weight sensing device 60 is configured to estimate the weight that the user uses when training. This may e.g. be implemented by measuring a distance between the weight sensing device 60 and an engaging member. One example implementation is shown in international patent application WO2017/178048. Then the broadcasted signal also comprises information about the estimated weight.

In conclusion, the at least one repetition detector 10 is configured to broadcast a short-range wireless communication signal comprising an identity of the exercise machine 1 and an indication of a vertical movement of at least one of the stacked weights 2.

The exercise machine identifier 40, also referred to as a "puck" (FIG. 5*a*), is configured to transmit a near field wireless communication signal comprising the identity of the exercise machine. More specifically, the exercise machine identifier 40 comprises a proximity detector e.g. a NFC receiver, configured to detect proximity of e.g. a user device 50 and a transmitter configured to transmit the near field wireless communication signal. The signal is e.g. NFC or RFID. The proximity detector and transmitter may be implemented by as an NFC tag. The near field wireless communication signal is typically received by a user device 50 (e.g. a user's smartphone). The user may then inform the server that he/she intends to start exercising in the exercise machine 1.

FIG. 5*b* illustrates the exercise machine identifier 40 and the repetition detector 10 when installed in the exercise machine 1. The repetition detector 10 is then mounted in the upper weight of the stacked weights 2.

Figure 4:
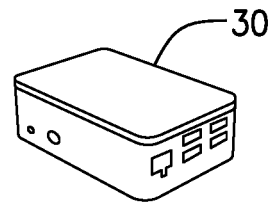
FIG. 4 illustrates an observer in further detail.

The observer 30 (FIG. 4) comprises a short-range wireless communication interface, for monitoring short range wireless communication signals transmitted by repetition detectors 10 arranged to a plurality of exercise machines in a gym. The observer 30 is the opposite of a broadcaster (here the repetition detector 10), i.e. it passively listens to broadcasting devices in its area and processes the data from the advertising packets it receives. It does not need a transmitter, as it sends nothing and is never meant to enter a connection.

The observer 30 is configured to receive signals broadcasted by repetition detectors 10 and to generate exercise data based on the received signals. More specifically, the observer 30 parses the data from detected advertisements (e.g. a series of integers) and sends it on the server 21. The observer 30 typically doesn't know whether a user is registered or logged in at the machines, it just forwards all correctly parsed advertisements. This means that all training in the gym is tracked, even when the user is not registered to the service. The observers 30 typically also comprise a securing arrangement for securing the observers e.g. to the ceiling.

The one or more observers 30 are typically placed centrally in the area to be able to monitor short-range wireless communication signals transmitted by all the exercise machines 1 in the gym. It is typically desirable to broadcast the short-range wireless communication signals with low power. Therefore, if there is a plurality of observers 30 they may be distributed to cover different rooms, floors etc. Note that several observers may hear the same broadcast. Then this needs to be resolved e.g. by the server 21.

Some analysis of the data is typically performed at the observer 30. More specifically, when the observer receives a pulse train from the repetition detector 10, then it filters the repetitions, e.g. removing duplicates having the same repetition number, and interprets it as one repetition. The generated exercise data is then forwarded to the server 21, where it is typically stored in the data storage 20. The observer 30 e.g. uses ordinary internet communication for communication with the server 21. The observer 30 may also comprise logic for establishing such connection and to detect bad internet connection and to reconnect, when connection is lost.

The data storage 20 is configured to store the exercise data of the exercise machines. In this embodiment, the data storage 20 is comprised in a server 21 or backend. Thus, the data storage 20 is e.g. a cloud implemented database or a remote database. The data stored in the data storage 20 may be used to gain insights and data about gym members and their training patterns and would also enable detailed analysis of utilization of gym machines.

The server 21 typically communicates over internet i.e. using IP/Ethernet. The server 21 will receive exercise data from the observer and store it in the data storage 20. The stored exercise data can be used for all kinds of analysis at a later point in time. If a user device 40 is registered on a certain machine, then exercise data will be forwarded to the user device 50 in real time. In other words, exercise data corresponding to every detected repetition will be forwarded to the user device 50.

Figure 6:
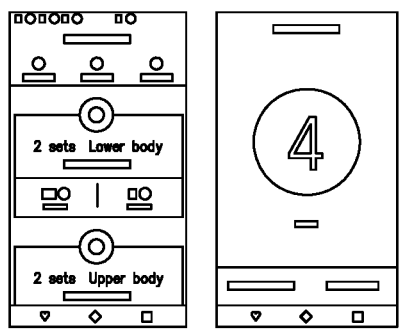
FIG. 6 illustrates a user interface of a user device.

The user device 50 is e.g. a smartphone comprising a mobile application, e.g. an android app (FIG. 6). In the mobile application, the user may monitor machine training automatically in real-time, follow pre-defined workouts or save your personal workouts, view history of all training data, workout programs, statistics and progress.

The user device 50 is configured to receive the near field wireless communication signal from the exercise machine identifier 40. The user device 50 is configured to communicate with the server 21 and to retrieve exercise data from the server 21.

The user device 50 may also inform the server 21 that it intends to start training in an exercise machine 1. In other words, the user device 50 is configured to register (log-in)/de-register (log-off) itself at the exercise machine 1.

When a user device 50 is registered at the exercise machine 1, the server 20 will then start forwarding exercise data to the user device 50 in real-time. In other words, the user device 50 is configured to retrieve, from the server 21, exercise data corresponding to an exercise machine identity comprised in the received near field wireless communication signal.

The user device 50 will present exercise data (or information associated therewith) to the user in any form depending on implementation. For example, the weight, the number of repetitions and the exercise machine's name are displayed on a display of the user device 50. In other words, the user device 50 is configured to provide the retrieved exercise data to a user. After completion of the exercising the entire program is typically sent to the server 21 for storage.

Figure 8:
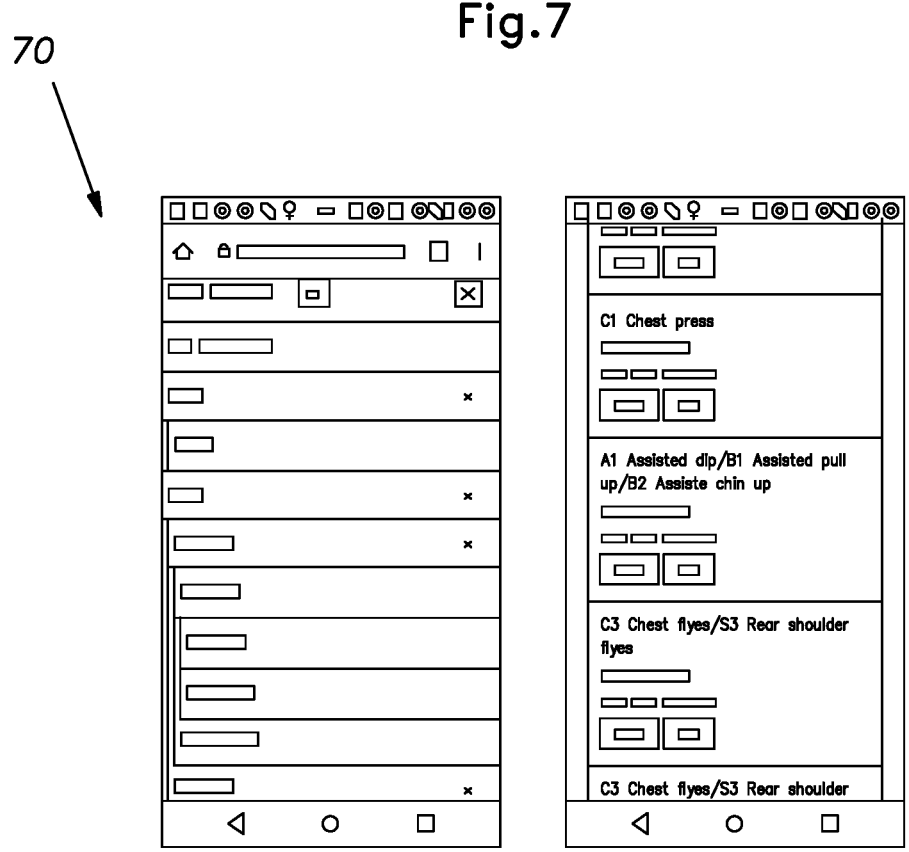
FIG. 8 illustrates a web interface that comprises an admin tool.

FIG. 8 illustrates a web interface that comprises an admin tool. The web interface can be used for accessing the server 21 for administration purposes.

Figure 9:
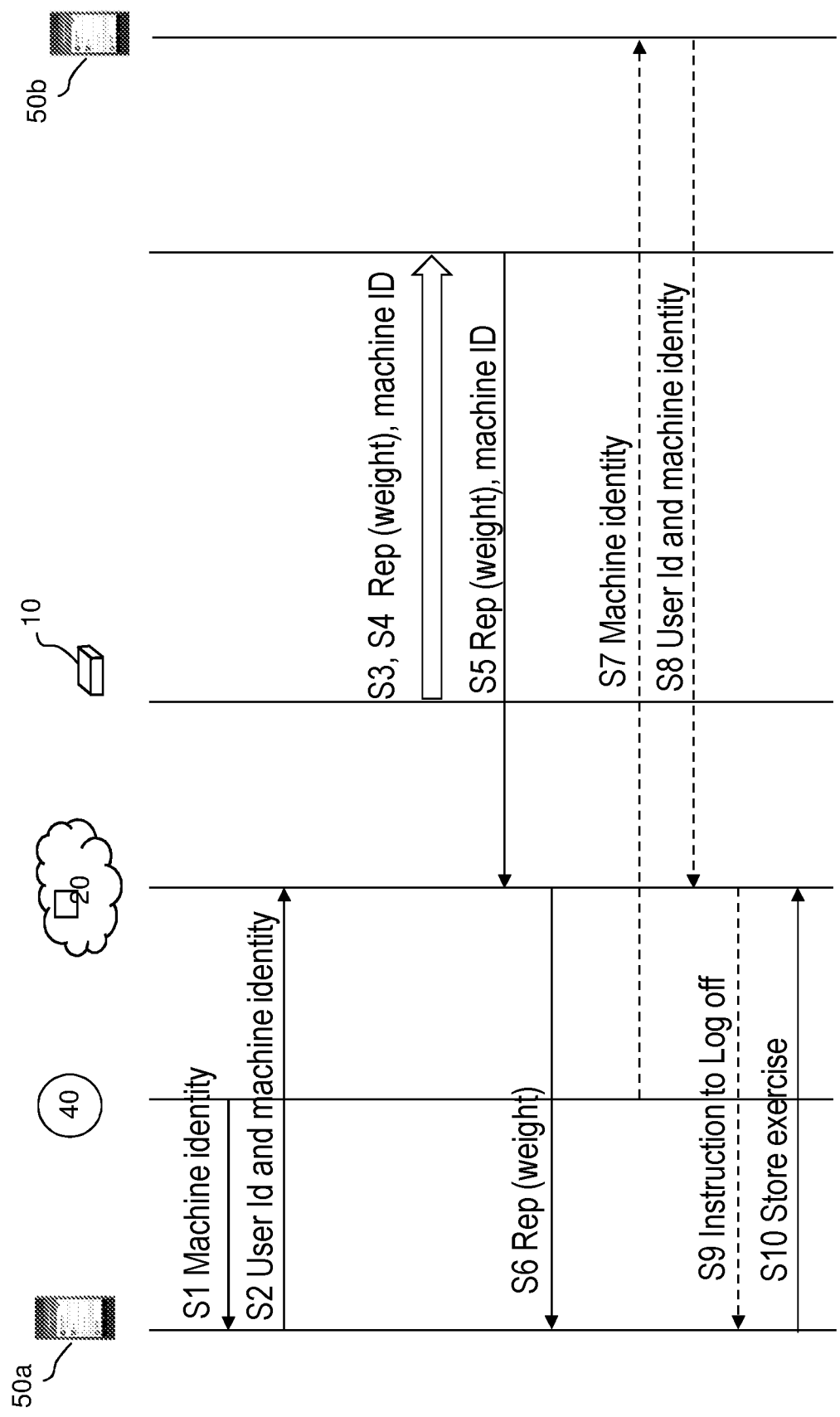
FIG. 9 illustrates signaling between the devices in the monitoring system according to the first example embodiment.

The operation of the system will now be described in further detail, with reference to the first example implementation of FIG. 2 and with reference to FIG. 9, which illustrates the signaling between the devices of the monitoring system 100. A user starts a workout (or follows a program), touches the exercise machine identifier 40 with his/her user device 50, does his/her exercises, touch another exercise machine identifier (not shown), does his/her exercises, and he/she is done. In real time, the weighs and repetitions are presented nicely and everything is logged for future reference.

The method is started when a first user device 50a (here first phone 50a) touches the exercise machine identifier 40 and is detected by the proximity sensor on the exercise machine identifier 40.

S1) The exercise machine identifier 40 then sends the exercise machine identity to the user device 50 with BLE. The exercise machine identifier 40 transmits at minimum power, so it only reaches the first phone 50a, which is close by. It is received by the first phone 50a if it's an iPhone. If it's an Android it reads the id by NFC.

S2) The user id that the user is logged in with is sent to the server 20 together with the exercise machine identity. The user is now registered at the exercise machine 1.

When the user starts a repetition (i.e. starts training), an accelerometer of the repetition detector 10 wakes up the repetition detector 10 from sleep mode. The Time of Flight sensor measures the distance to the top of the exercise machine. When the repetition detector is back to starting position for a few seconds it goes to sleep again.

When the cable which lifts the weight pack, it is stretched (this is a way to ensure consistency in measurements), the distance toward the pin is measured with another time of flight sensor. This distance represents a weight.

S3) The observer broadcasts a short-range wireless communication signal comprising machine ID and repetitions. The repetitions are sent constantly (i.e. in real time, one by one) as they occur to the observer via BLE. The weight is only sent once to the observer 30 via BLE.

S4) The observer 30 is positioned centrally in the gym, and there can be more than one observer 30 in a gym. The observers receive the packages from the exercise machine(s) in the gym.

S5) The observer 30 sends the received repetition information on to the server 21.

S6) The server 21 knows which user is at what machine (due to registration S2) and sends the repetitions and weight further to the first phone 10 which presents it to the user.

A second user device 50b (second phone 50b) touches the exercise machine identifier 40 when exercise machine identifier 1 is still logged in on the exercise machine. It is detected by the exercise machine identifier.

S7) The exercise machine identity is sent to the second phone 50b (same as S1)

S8) Second phone 50b sends the user id that the user is logged in with to the server 21, with the exercise machine identity (same as S2)

S9) The server 21 tells the second phone 50b to log off from the exercise machine 1. A user can also log off from an exercise machine by touching another exercise machine identifier, or in the user interface, UI.

S10) The entire exercise is stored, once the set or the entire exercise is completed.

This example implementation solution is dependent upon a good internet, since the real-time experience is delivered over internet. With a local connectivity based solution it is possible get away from the problem. If the internet is lagging in the connection from the observer to the cloud, or from the cloud to the phone, the user experience will be bad.

Figure 10:
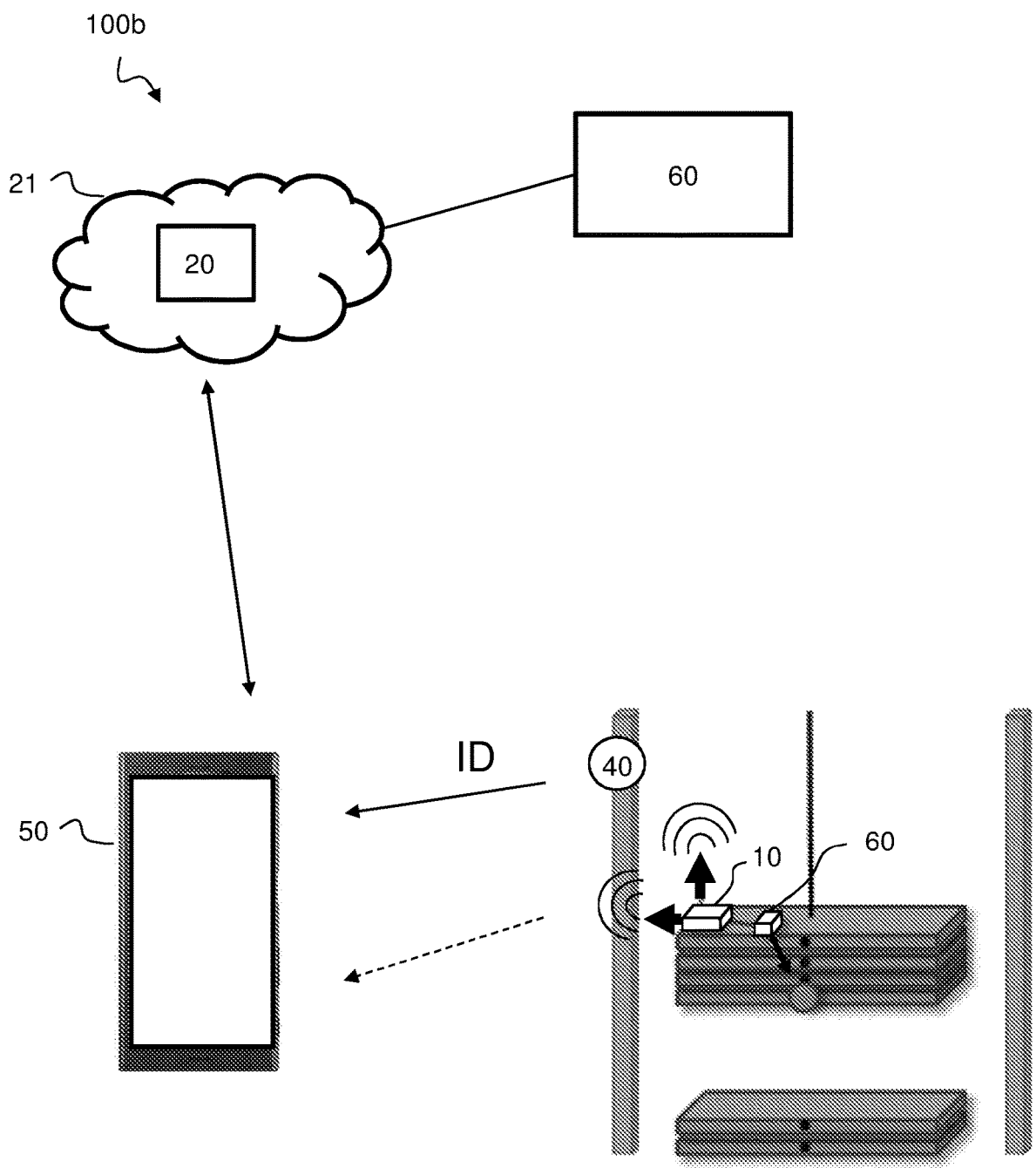
FIG. 10 illustrates a second example embodiment of the monitoring system.

FIG. 10 illustrates a second example embodiment (denoted 100b) of the monitoring system 100. This embodiment differs from the first example embodiment in that the functionality of the observer 30 is integrated in the user device 50, e.g. the user's phone. This means that during exercise the signaling to from a server 21 over internet is not needed. This embodiment could be used on its own, when there is no wireless communication network coverage or it may be used in parallel with the first embodiment to enhance security, as will be explained in more detail below.

The repetition detector 10, the exercise machine identifier 40 will be the same as in the first example embodiment. However, the functionality of the observer 30 and the user device 50 would typically be different, as no signaling there between is needed. In particular the integrated observer functionality will provide the exercise data directly to the user device 50, as it is comprised therein. Furthermore, the user device 50 will be configured to, when occupied, broadcast a signal that informs other user devices that the exercise machine 1 is occupied.

Figure 11:
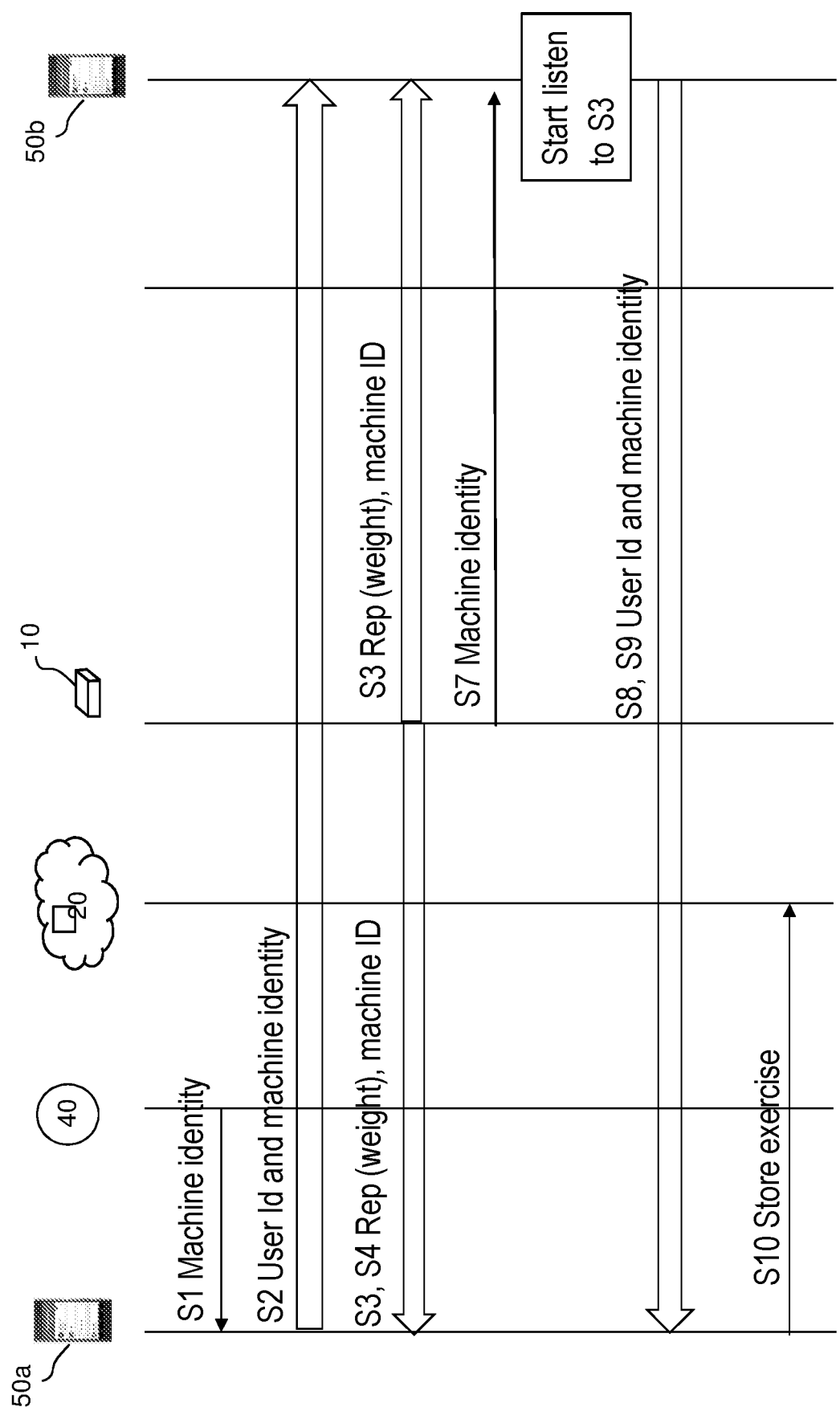
FIG. 11 illustrates signaling between the devices in the monitoring system according to the second example embodiment.

FIG. 11 illustrates signaling between the devices in the monitoring system 100 according to the second example embodiment 100b.

The method is initiated when the first user device 10a (first phone) touches the exercise machine identifier 40, and is detected by the proximity sensor on the exercise machine identifier 40.

S1) The exercise machine identifier 40 then sends the exercise machine identity of the exercise machine 1 with BLE to the first phone 50a. It transmits at minimum power, so it only reaches the first phone 50a which is close by. It is received by the first phone if it's an iPhone. If it's an Android the first phone reads the id by NFC.

S2) The first phone 50a starts to listen to the repetition detector 10 of the exercise machine 1. The first phone 50a also broadcasts to all other phones a signal instructing them to stop listening to this machine (i.e. the exercise machine with the received the exercise machine identity).

As in the first example embodiment, the accelerometer of the repetition detector 10 wakes up the system from sleep mode, when the user starts a repetition. The Time of Flight sensor measures the distance to the top of the exercise machine. When the repetition detector 10 is back to starting position for a few seconds it goes to sleep again. When the cable which lifts the weight pack, it is stretched (this is a way to ensure consistency in measurements) the distance toward the pin is measured with another time of flight sensor. This distance represents a weight.

S3) The repetition detector 10 continuously broadcasts detected repetitions (i.e. in real-time) via BLE. The weight is sent once via BLE. The first phone 50a which listens to the exercise machine receives the detection and weight information and presents it to the user. In other words, the user device 40 monitors for a short-range wireless communication signal comprising the exercise machine ID received in step S2.

S4) The short-range wireless communication signal is monitored directly by the observer 30 comprised in the user device 50.

Steps S5, S6 of the first example embodiment are not needed in this example implementation, as the short-range wireless communication signal is monitored directly by the user device 50. The filtering of processing of the repetitions and weight is handled internally in the user device 50. Instead, the exercise data is generated and stored internally in the first user device 50.

When a second user device 50b (second phone) touches the exercise machine identifier it is detected by the proximity sensor. (same as step S1).

S7) The exercise machine identity is then sent to the second phone 50b, same as step S2).

S8) Phone 50b starts to listen to the short-range wireless communication signal broadcasted S3) by the repetition detector 10 of the exercise machine 1. Note, that the second phone 50b can hear the signal all the time, but now it starts to actively listen to it. Phone 50b also broadcasts to all other phones stop listening to the exercise machine. The first phone 50a can also be logged out from an exercise machine by touching another exercise machine identifier, or directly in the UI.

S9) The first phone 50a receives the broadcasted signal which serves as an indication for the first user device to log off the exercise machine 1. The first user may be automatically logged off or may be prompted to log off.

S10) The first and second phones 10a, 10b can backup or store the exercise in the remote the data storage 20, but is not necessary. The monitoring system 100b can run without a data storage or data may be uploaded at a later point in time, when connection has been established.

In the drawings and specification, there have been disclosed exemplary aspects of the disclosure. However, many variations and modifications can be made to these aspects without substantially departing from the principles of the present disclosure. Thus, the disclosure should be regarded as illustrative rather than restrictive, and not as being limited to the particular aspects discussed above. Accordingly, although specific terms are employed, they are used in a generic and descriptive sense only and not for purposes of limitation.

The description of the example embodiments provided herein have been presented for purposes of illustration. The description is not intended to be exhaustive or to limit example embodiments to the precise form disclosed, and modifications and variations are possible in light of the above teachings or may be acquired from practice of various alternatives to the provided embodiments. The examples discussed herein were chosen and described in order to explain the principles and the nature of various example embodiments and its practical application to enable one skilled in the art to utilize the example embodiments in various manners and with various modifications as are suited to the particular use contemplated.

It is, for example, possible to combine the embodiments and let the user device 50 receive the exercise data both from the server 21 and directly from the repetition detector 10. In other words, in some embodiments the functionality of the observer 30 is also comprised in the user device 50, which means that the user device 50 can receive exercise data directly from the repetition detector 10.

In other words, in some embodiments the user device 50 is configured to retrieve broadcasted exercise data both from the server 21 and directly from the repetition detector 10 and to combine exercise data received directly from the repetition detector 10 with exercise data retrieved from the server 21.

For example, the user device 50 may receive two parallel streams of advertisements (here referred to as advertising messages) that originate from (i.e. are broadcasted by) one specific repetition detector 10, where each advertising message comprises an exercise machine identifier and a message identifier (e.g. 001, 002, 003). The user device 50 may then compare the individual messages to determine which advertising messages were actually broadcasted by the repetition detector 10. The redundancy created by using two streams, decreases the risk that individual advertising message is missed or incorrectly received. In other words, this solution would typically be more stable, as the risk that an individual packet is lost is decreased. For example, if the internet connection is lost, the user device 50 will continue to receive exercise data directly from the repetition detector 10.

The features of the embodiments described herein may be combined in all possible combinations of methods, apparatus, modules, systems, and computer program products. It should be appreciated that the example embodiments presented herein may be practiced in any combination with each other.

It should be noted that the word "comprising" does not necessarily exclude the presence of other elements or steps than those listed and the words "a" or "an" preceding an element do not exclude the presence of a plurality of such elements. It should further be noted that any reference signs do not limit the scope of the claims, that the example embodiments may be implemented at least in part by means of both hardware and software, and that several "means", "units" or "devices" may be represented by the same item of hardware.

The various example embodiments described herein are described in the general context of method steps or processes, which may be implemented in one aspect by a computer program product, embodied in a computer-readable medium, including computer-executable instructions, such as program code, executed by computers in networked environments. A computer-readable medium may include removable and non-removable storage devices including, but not limited to, Read Only Memory (ROM), Random Access Memory (RAM), compact discs (CDs), digital versatile discs (DVD), etc. Generally, program modules may include routines, programs, objects, components, data structures, etc. that performs particular tasks or implement particular abstract data types. Computer-executable instructions, associated data structures, and program modules represent examples of program code for executing steps of the methods disclosed herein. The particular sequence of such executable instructions or associated data structures represents examples of corresponding acts for implementing the functions described in such steps or processes.

Figure 12:
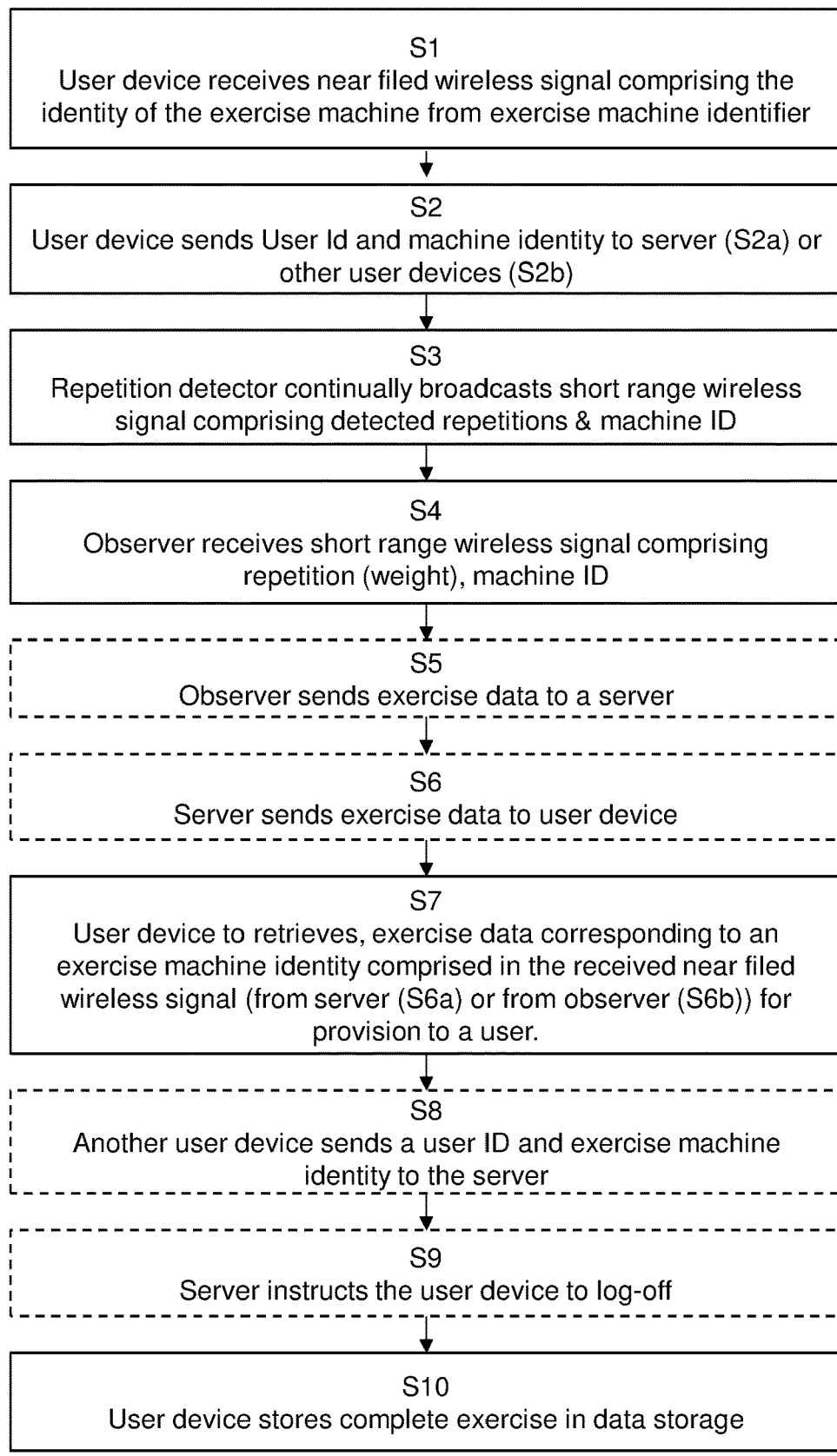
FIG. 12 illustrates a method for monitoring a plurality of exercise machines.

FIG. 12 illustrates a corresponding method for monitoring a plurality of exercise machines. The method is typically performed when a user is exercising in a gym. The user will typically initiate the method by starting the application, logging in (which might be automatic) and then tap the user device 50 (typically a smart phone) at the exercise machine identifier 40 he intends to use.

In step S1 the user device 50 receives near filed wireless communication signal comprising the identity of the exercise machine from exercise machine identifier 40. In other words, the user device is informed about the identity of the exercise machine that he/she intends to use.

In step S2 the user device 50 sends User Id and machine identity to server S2a and/or to other user devices S2b. As explained above, the user may register to the machine either by informing the server or by directly informing other user devices.

In step S3 the repetition detector 10 continually broadcasts short range wireless communication signal comprising detected repetitions and machine ID and typically also weight and repetition/sequence number.

In step S4 the observer receives a short-range wireless communication signal transmitted by the repetition detector 10 comprising information about a detected repetition (and potentially also weight) and machine ID. As explained above the observer typically identifies a repetition using e.g. filtering.

In the optional step S5 (used in a server implementation) the observer 30 forwards exercise data corresponding to the received signal to a server 21.

In the optional step S6 (used in a server implementation) the server 21 sends exercise data to user device 50 of a user that has registered to the corresponding exercise machine 1.

In step S7 the user device to retrieves, exercise data corresponding to an exercise machine identity comprised in the received near filed wireless communication signal from server S6a or from observer S6, for provision to a user.

In the optional step S8 another user device sends a user ID and exercise machine identity to the server.

In the optional step S9 the server or the other user device instructs the user device to log-off and/or to stop listening to the repetition detector 10.

In the optional step S10 the user device stores complete exercise in a data storage 20. This might be done when changing machine or when the entire exercise is completed.

The invention claimed is:

1. A monitoring system for monitoring a plurality of exercise machines arranged in a gym, the monitoring system comprising:
   a main unit configured to be arranged at a plurality of stacked weights of a first exercise machine of the plurality of exercise machines and being operable to broadcast a short-range wireless communication signal comprising main unit exercise data representative of: i) an exercise machine identity of the first exercise machine, and ii) an indication of a vertical movement of at least one of the plurality of stacked weights;
   an exercise machine identifier device configured to transmit a near field wireless communication signal comprising the exercise machine identity of the first exercise machine;
   an observer device configured to be arranged in the gym to receive the short-range wireless communication signal broadcasted by the main unit and to generate observer device exercise data for the first exercise machine based on the received short-range wireless communication signal;
   a server operatively coupled with a data storage, the server being configured to receive the observer device exercise data for the first exercise machine from the observer device and to store the received exercise data for the first exercise machine in the data storage; and
   observer program code executable by an associated user device to cause the associated user device to:
      receive the near field wireless communication signal comprising the exercise machine identity of the first exercise machine;
      receive from the server the observer exercise data corresponding to the first exercise machine identified by the exercise machine identity;
      selectively broadcast a signal that informs other associated user devices arranged in the gym that the first exercise machine of the plurality of exercise machines is occupied based on the associated user device receiving the near field wireless communication signal comprising the exercise machine identity of the first exercise machine;
      receive the main unit exercise data from the main unit;
      create redundant exercise data by combining the observer device exercise data with the main unit exercise data; and
      present the redundant exercise data corresponding to the first exercise machine identified by the exercise machine identity, or information associated with the redundant exercise data, to an associated user of the associated user device.

2. The monitoring system according to claim 1 further comprising:
   a weight sensing device configured to sense a weight of the plurality of stacked weights that perform the vertical movement,
   wherein the short-range wireless communication signal further comprises an indication of the sensed weight.

3. The monitoring system according to claim 1, wherein the associated user device is configured to provide functionality of the observer device to retrieve the observer device exercise data broadcasted from the server.

4. The monitoring system according to claim 1, wherein the associated user device is configured to provide functionality of the observer device to receive the main unit exercise data directly from the main unit.

5. The monitoring system according to claim 4, wherein the associated user device is configured to provide functionality of the observer device to present to the associated user of the associated user device a combination of exercise data received directly from the observer with exercise data received from the server.

6. The monitoring system according to claim 1, wherein the observer device is configured to generate the observer device exercise data in real-time and wherein the associated user device is configured to provide functionality of the observer device to retrieve the generated observer device exercise data and to present it to the associated user of the associated user device in real-time.

7. The monitoring system according to claim 1, wherein the associated user device is configured to provide functionality of the observer device to present the redundant exercise data on a display of the associated user device.

8. The monitoring system according to claim 1, wherein the exercise machine identifier device is configured to transmit the near field wireless communication signal as an NFC signal.

9. The monitoring system according to claim 1, wherein the main unit is operable to broadcast the short-range wireless communication signal as a low energy signal.

10. The monitoring system according to claim 1, wherein the main unit is operable to broadcast the short-range wireless communication signal as a low energy near field wireless signal.

11. The monitoring system according to claim 1, wherein the observer program code executable by the associated user device comprises observer program code executable by an associated smartphone.

12. A method for monitoring a plurality of exercise machines arranged in a gym, wherein each of the exercise machines comprise a plurality of stacked weights, wherein each stacked weight comprises a main unit continually broadcasting a short-range wireless signal comprising an exercise machine identifier and an indication of a vertical movement of at least one of the stacked weights, the method comprising:
   executing observer program code by an associated user device to receive a near filed wireless communication signal transmitted by a first exercise machine of the plurality of exercise machines, the received near filed wireless communication signal comprising main unit exercise data representative of an exercise machine identity of the first exercise machine;

executing the observer program code by the associated user device to send a user identity and the exercise machine identity of the first exercise machine to a server and/or to other user devices;

receiving, by one or more observers arranged centrally in the gym, the short-range wireless signals broadcasted by the main units of the plurality of exercise machines;

sending from the one or more observers, observer device exercise data generated based on the received short-range wireless signals, to the server;

executing the observer program code by the associated user device to receive from the server the observer device exercise data corresponding to the exercise machine identity of the first exercise machine comprised in the received near filed wireless signal for provision to a user;

executing the observer program code by the associated user device to selectively broadcast a signal that informs other associated user devices arranged in the gym that the first exercise machine of the plurality of exercise machines is occupied based on the associated user device receiving the near field wireless communication signal comprising the exercise machine identity of the first exercise machine;

executing the observer program code by the associated user device to receive the main unit exercise data from the first exercise machine;

executing the observer program code by the associated user device to create redundant exercise data by combining the observer device exercise data with the main unit exercise data; and executing the observer program code by the associated user device to present the redundant exercise data corresponding to the first exercise machine identified by the exercise machine identity, or information associated with the redundant exercise data, to an associated user of the associated user device.

13. The method of claim 12, wherein the executing the observer program code by the associated user device to retrieve the exercise data comprises retrieving the exercise data from the server and/or directly from a repetition detector of the exercise machine corresponding to the exercise machine identity.

14. The method of claim 13 further comprising, combining exercise data received directly from the observer with exercise data received from the server.

* * * * *